(12) United States Patent
O'Lenick, Jr. et al.

(10) Patent No.: US 6,861,542 B1
(45) Date of Patent: Mar. 1, 2005

(54) DIMER AMIDOPROPYL DIMETHYL QUATERNARY COMPOUNDS

(75) Inventors: Anthony J. O'Lenick, Jr., Dacula, GA (US); Thomas G. O'Lenick, Dacula, GA (US)

(73) Assignee: SurfaTech Corporation, Dacula, CA (US)

( * ) Notice: Subject to any disclaimer, the term of this patent is extended or adjusted under 35 U.S.C. 154(b) by 0 days.

(21) Appl. No.: 10/765,602

(22) Filed: Jan. 28, 2004

(51) Int. Cl.$^7$ ............................................. C07C 233/05

(52) U.S. Cl. ............................ 554/35; 554/37; 564/152

(58) Field of Search ....................... 554/35, 37; 564/152

(56) References Cited

U.S. PATENT DOCUMENTS 6,331,293 B1  12/2001  Smith et al.

FOREIGN PATENT DOCUMENTS

JP          4-202336      *   7/1992

* cited by examiner

*Primary Examiner*—Shailendra Kumar

(57) ABSTRACT

The present invention relates to a class of compounds having specific quaternized amine based upon a dimer acid amido amine linked to specific phosphate esters. Dimer acid is a C-36 diacid having a cyclic structure and two amine groups that allow for the synthesis of a high molecular weight material quaternary compound which is extremely substantitive to human skin and are well tolerated by human tissue making them suitable for use preparation of barrier products for personal care applications.

7 Claims, No Drawings

DIMER AMIDOPROPYL DIMETHYL QUATERNARY COMPOUNDS

FIELD OF THE INVENTION

The present invention relates to a novel class of compounds having specific quaternized amine based upon a dimer acid amido amine quaternary compound. Dimer acid is a C-36 diacid having a cyclic structure and two amine groups that allow for the synthesis of a high molecular weight cationic compound which is extremely substantitive to human skin and are well tolerated by human tissue making them suitable for use preparation of barrier products for personal care applications.

BACKGROUND OF THE INVENTION

It is very desirable to provide a material from aqueous solution that will condition the hair and still be compatible with anionic surfactants. This allows for the preparation of clear two in one shampoo systems, clear 2 in one shower gels, and clear two in one bath products. By two in one products in meant, a product that contains both anionic surfactant, most commonly sulfates and ether sulfates and a cationic conditioning agent. The anionic surfactant is the detergent, which cleans the hair or skin, and the cationic product is for conditioning providing softness, slip and feels to the skin. The problem with such product has always been the incompatibility of the anionic and cationic surfactants with each other. When many of these products are present in the same solution an insoluble salt forms making a cosmetically unacceptable white gunk that does not stay in solution.

As will become clear, by making a very large molecule the present invention results in a we call a soft quaternary compound. By soft quaternary compound is meant one that not withstanding its cationic charge is of a structure so that when placed in water along with the anionic surfactant, a clear stable solution is obtained. Surprisingly, because of the high molecular weight of the quaternary compound, the deposition on the hair and skin is increased. While not wanting to be held to only one mechanism, we believe there rather than a precipitate observed with so-called hard quarts, compounds of the present invention form a self-assembling complex between the anionic and cationic surfactant. This complex, while water-soluble is large enough to disrupt hydrogen bonding between water molecules, and as such energetically, the complex will be deposited on the skin or hair leaving the remaining solution at the lowers free energy level.

The self-assembling aspect of the present invention, which we believe is the result of orientation of the salt of the cationic compounds of the present invention and the anionic surfactants present in solution, can be demonstrated by the fact that upon initial mixing of the components, a hazy or cloudy dispersion occurs. With suitable mixing, this hazy dispersion becomes a solution and the viscosity increases.

The compounds of the present invention can be formulated into body washes and other skin products and hair care products to provide a "delivery system" for conditioning the hair or skin. The high molecular weight of the quart and the fact that the point. charges are far apart in the molecule results in through and efficient deposition on the hair or skin. This provides uniformity of conditioning agent over the entire hair of skin surface. This is particularly important for applications on hair for people with long hair. In general the long hair has at it's tip areas that are more damaged, dry and in need of conditioning. The hair closest to the scalp is newer, less damaged, and less in need of conditioning. This dichotomy of hair condition is more effectively treated by the complexes formed by the current invention than by other quarts. In addition, the di-nature of the compounds provides for outstanding substantivity of the molecule allow for very mild natural like materials that can be used in products where low irritation is important.

U.S. Pat. No. 6,331,293 issued Dec. 18, 2001 to Smith et al describes phosphobetaines that are derived from dimer acid. Unlike the compounds of the present invention, these materials, are anphoteric surfactants and are barriers when applied to the skin. It is stated that the compounds are "extremely substantitive to human skin and are well tolerated by human tissue making them suitable for use preparation of barrier products for personal care applications". Unlike these materials, the compounds of the present invention are not amphoterics, but are quarts, are not barriers but are conditioning agents that do not build up on the hair or skin.

SUMMARY OF THE INVENTION

Objective of the Invention

It is the objective of the invention to provide a novel dimer acid based amido quaternary compounds and a process of its use which comprises contacting the skin with an effective conditioning concentration of the novel quaternary compounds when applied in aqueous solution containing anionic surfactants. These anionic surfactants are preferably fatty sulfates and fatty ether sulfates having between 1 and 4 moles of ethylene oxide present.

In accordance with the present invention, we have now been discovered novel quaternary compound, which conforms to one of the following structures:

The first structure is:

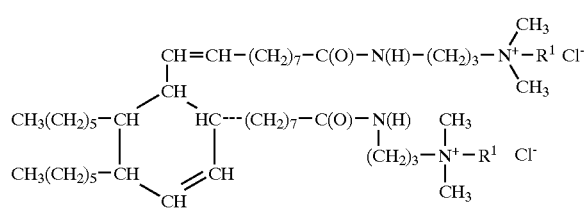

wherein;

$R^1$ is selected from the group consisting of —$CH_3$, —$CH_2$-CH(OH)$CH_2$OH and

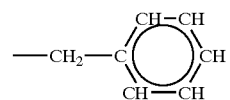

The second closely related structure is:

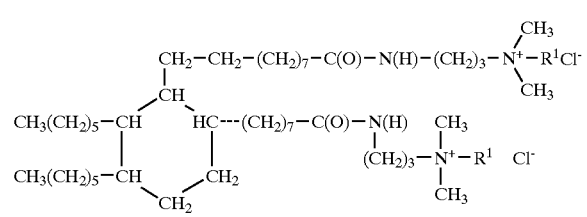

wherein;

$R^1$ is selected from the group consisting of —$CH_3$, —$CH_2$-CH(OH)$CH_2$OH and

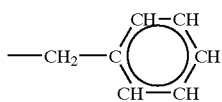

The difference between the two is the second has no double bond in the cyclic structure, while the first has a double bond. The double bond is removed by hydrogenation of the acid prior to making the quaternary compound. This variation has lighter color and better oxidative stability, making it prized for cosmetic applications where a water white product is desired. Consumers consider water white products as cleaner and more appealing over yellow products.

The present invention is also directed to a process for very efficiently conditioning the skin and hair from aqueous solution containing anionic surfactant. The complex that forms is very efficient in providing conditioning and can be used at concentrations as low as 0.5% by weight in a shampoo formulation. This is very important in products where low irritation is important like baby shampoo and bubble bath products.

Preferred Embodiments

In a preferred embodiment $R^1$ is —$CH_3$.

In a preferred embodiment, $R^1$ is —$CH_2$—$CH(OH)CH_2OH$.

In a preferred embodiment $R^1$ is

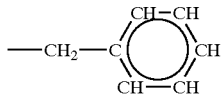

DETAILED DESCRIPTION OF THE INVENTION

The present invention is directed to novel cationic compounds, which conform to one of the following structure:

The first structure is:

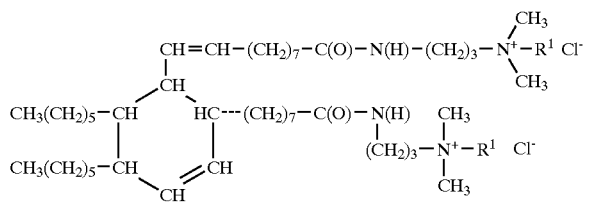

wherein;
  $R^1$ is selected from the group consisting of —$CH_3$, —$CH_2$—$CH(OH)CH_2OH$ and

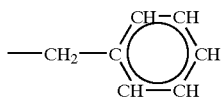

The second closely related structure is:

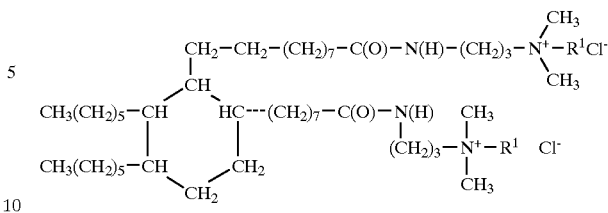

wherein;
  $R^1$ is selected from the group consisting of —$CH_3$, —$CH_2$—$CH(OH)CH_2OH$ and

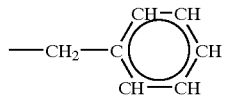

The compounds of the present invention are prepared by reacting first reacting dimer acid with dimethylaminopropyl amine (DMAPA) to give a tertiary amine intermediate.

The first structure is:

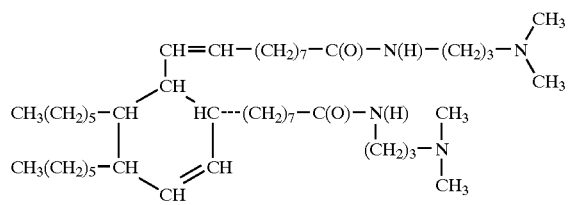

wherein;
  $R^1$ is selected from the group consisting of —$CH_3$, —$CH_2$—$CH(OH)CH_2OH$ and

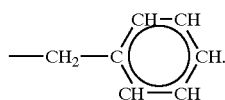

The second closely related structure is:

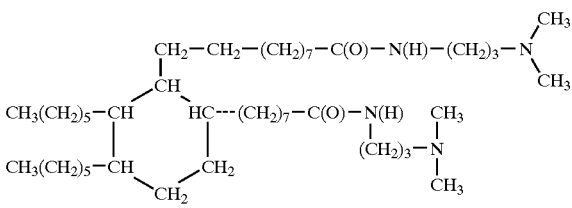

wherein;
  $R^1$ is selected from the group consisting of —$CH_3$, —$CH_2$—$CH(OH)CH_2OH$ and

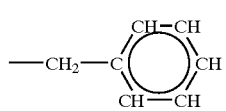

In a subsequent step, the dimer DMAPA product is reacted with methyl chloride or chloroglycerin to give the compounds of the present invention.

The compounds of the present invention are made reaction of the methyl chloride or chloro glycerin under aqueous conditions. The product of the invention is thereby attained.

The compatibility of this novel quaternary compounds of the invention with human tissue, i.e., dermal and eye tissue has also been tested. In these tests, 48-hour human patch dermal evaluations (5% in water), in vitro ocular evaluations (3% in water) and repeated insult patch tests (3% in water) determined that the compounds are substantially non-irritating to humans, they are safe and suitable for use in eye area products and are not a skin sensitizer to humans.

EXAMPLES

Dimer Acid and Hydrogenated Diner Acid

Dimer acid and hydrogenated dimer acid are items of commerce commercially available from several suppliers, one of which is Cognis Corporation, formerly the Emery Division of Henkel.

Dimer acid conforms to the following structure;

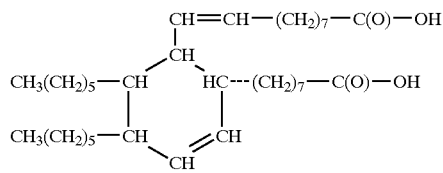

Hydrogenated dimer acid conforms to the following structure;

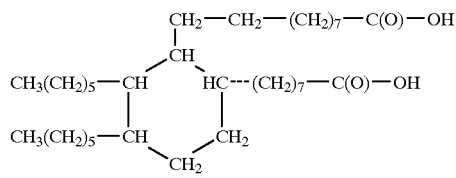

DMAPA

Dimethylaminopropyl Amine is an item of commerce available from a variety of sources including Dow Chemical.

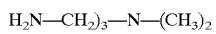

Chloroglycerin

Chloroglycerin is a item of commerce available from a variety of sources including Dixie Chemical and Phoenix Chemical of Somerville, N.J. It conforms to the following structure:

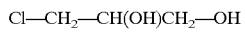

Methyl Chloride

Methyl chloride is an item of commerce and is available from a variety of sources. It conforms to the following structure:

Benzyl Chloride

Benzyl Chloride is an item of commerce and conforms to the following structure:

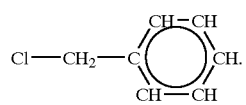

Example 1

Preparation of Dimer Amido Amine

To 561.0 grams if dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm. The product is a yellow water insoluble liquid at ambient temperatures.

Example 2

Preparation of Dimer Amido Amine

To 563.0 grams if hydrogenated dimer acid is added 153.0 grams of dimethylaminopropyl amine. The mixture is heated to 180–200° C. and held for 3–8 hours. Once the temperature begins to reach 180° C., water begins to distill off. An excess of dimethylaminopropyl amine is added to speed up the reaction. When the acid value reaches 1.0 mg KOH/gram, the excess dimethylaminopropyl amine is stripped off by applying vacuum. The resulting product is the dimer amido amine useful as an intermediate in the preparation of the compounds of the present invention. The alkali value of the product so produced is 180.0 mg KOH/gm.

Example 3

Preparation of the Cationic of the Present Invention

Into a suitable reaction flask is charged 937.0 grams of de-ionized water. Next, add 288.0 grams of chloroglycerin. Heat is applied to 90° C. Next, 625.0 grams of dimer amidoamine (example 1) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Example 4

Preparation of the Cationic of the Present Invention

Into a suitable reaction flask is charged 937.0 grams of de-ionized water. Next, add 288.0 grams of chloroglycerin.

Heat is applied to 90° C. Next, 625.0 grams of dimer arnidoanine (example 2) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Example 5

Preparation of the Cationic of the Present Invention

Into a suitable reaction flask is charged 937.0 grams of de-ionized water. Next, add 135.0 grams of benzyl chloride. Heat is applied to 90° C. Next, 625.0 grams of dimer amidoamine (example 1) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

The compound of the present invention is used without additional purification. It is a clear viscous liquid and is sold as an aqueous solution of between 30 and 40% solids by weight.

Example 6

Preparation of the Cationic of the Present Invention

Into a suitable reaction flask is charged 937.0 grams of de-ionized water. Next, add 135.0 grams of benzyl chloride. Heat is applied to 90° C. Next, 625.0 grams of dimer amidoamine (example 2) are charged into the reaction vessel under good agitation. The temperature is maintained at between 90° C. and 95° C., until the percentage of free tertiary amine is 0.5% maximum. During the reaction time, the pH is kept at between 7 and 8 with NaOH as required. The reaction mass will clear when the product is at 90 C for about 1 hour. The reaction time is approximately 6 to 9 hours. The % NaCl is monitored and the reaction is deemed complete when the % of theoretical NaCl reaches 98%.

Example 7

Preparation of the Cationic of the Present Invention

In a stainless Parr autoclave was added 625 grams of dimer amidoamine (example 1), 10.7 grams of sodium bicarbonate, and 200 grams of isopropanol. The autoclave is sealed, agitation applied and a nitrogen purge applied. The temperature is raised to 85° C. Charge 114.8 grams of methyl chloride slowly, so that the temperature is maintained between 80° C. and 90° C. After all the methyl chloride is added, keep the temperature at 80° C. for two hours under agitation. Cool down and filter. The product is used without additional purification.

Example 8

Preparation of the Cationic of the Present Invention

In a stainless Parr autoclave was added 627 grams of dimer amidoamine (example 2), 10.7 grams of sodium bicarbonate, and 200 grams of isopropanol. The, autoclave is sealed, agitation applied and a nitrogen purge applied. The temperature is raised to 85° C. Charge 114.8 grams of methyl chloride slowly, so that the temperature is maintained between 80° C. and 90° C. After all the methyl chloride is added, keep the temperature at 80° C. for two hours under agitation. Cool down and filter. The product is used without additional purification.

Applications Examples

The compounds of the present invention show good compatibility with anionic surfactants, are very substantive particularly at low concentrations. In order to demonstrate this the compounds of the present invention were compared to a variety of other cationic materials.

Anionic Compatibility Testing

Solution A

The compounds evaluated were diluted to 10% solids with DI water before evaluation.

Solution B

A solution of 10% b weight sodium lauryl sulfate was prepared. The sodium lauryl sulfate was obtained from Colonial Chemical in South Pittsburgh Tennessee.

Anionic Compatibility Test 100 ml of solution B was added to a 400 ml beaker. Solution A was slowly added until either a precipitate or haziness was noted. The number of ml of solution was recorded at the first point the haze of precipitate was noted. That point was noted as the end point. The higher the volume used to the end point the better the compatibility. The test is stopped at 100 ml at which point the product is considered fully compatible.

| Products of the present invention | | | |
|---|---|---|---|
| Example | Description | | |
| 3 | Dimer glyceryl quat | 100.0 ml | Fully |
| 4 | Hydrogenated dimer glyceryl quat | 100.0 ml | Fully |
| 5 | Dimer benzyl quat | 88.2 ml | Very |
| 6 | Hydrogenated dimer benzyl quat | 87.0 ml | Very |
| 7. | Dimer tri-methyl quat | 58.9 ml | Compatible |
| 8. | Hydrogenated dimer tri-methyl | 59.6 ml | Compatible |

| Comparison products (Not of this invention) | | |
|---|---|---|
| Cetyl trimethyl benzyl ammonium chloride | 0.5 ml | Very Incompatible |
| Stearyl dimethyl denzalkonium chloride | 1.0 ml | Very Incompatible |
| Stearylamidopropyl dimethyl ammonium chloride | 20.0 ml | mildly compatible |

Since only stearylamidopropyl dimethyl ammonium chloride was even mildly compatible, it was evaluated against the compounds of the present invention at 0.5% active by weight in commercial baby shampoo.

The baby shampoo compounds were evaluated on 10 people with half head studies. The values reported were the average rounded to the nearest whole number. The results clearly show that only the compounds of the present invention provide measurable conditioning effects.

The scale used to evaluate was:

| Conditioning effect | Description |
|---|---|
| 1 | no conditioning |
| 2 | minimal conditioning |
| 3 | measurable conditioning |
| 4 | good conditioning |
| 5 | excellent conditioning |

| Example | Description | Conditioning Value |
|---|---|---|
| 3 | Dimer glyceryl quat | 4 |
| 4 | Hydrogenated dimer glyceryl quat | 4 |
| 5 | Dimer benzyl quat | 5 |
| 6 | Hydrogenated dimer benzyl quat | 5 |
| 7. | Dimer tri-methyl quat | 4 |
| 8. | Hydrogenated dimer tri-methyl | 4 |
|  | Stearylamidopropyl dimethyl ammonium chloride | 1 |
|  | Baby Shampoo Control | 1 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

What is claimed is:

1. A quaternary compound conforming to the following structure:

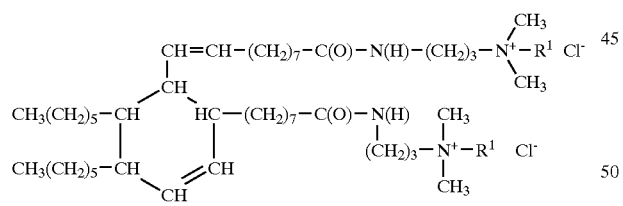

wherein;

$R^1$ is selected from the group consisting of —$CH_3$, and

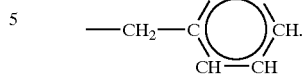

2. A quaternary compound or claim 1 wherein $R^1$ is —$CH_3$.

3. A quaternary compound of claim 1 wherein $R^1$ is

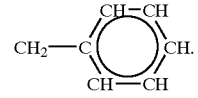

4. A quaternary compound conforming to the following structure:

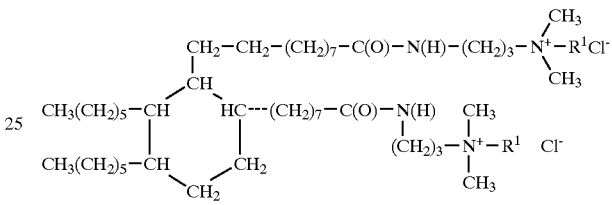

wherein;

$R^1$ is selected from the group consisting of —$CH_3$, —$CH_2$—$CH(OH)CH_2OH$ and

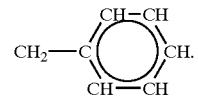

5. A quaternary compound of claim 4 wherein $R^1$ is —$CH_3$.

6. Quaternary compound of claim 4 wherein $R^1$ is —$CH_2$—$CH(OH)CH_2OH$.

7. A quaternary compound of claim 4 wherein $R^1$ is

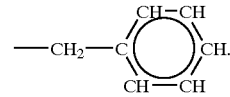

* * * * *